United States Patent [19]

Pelcher

[11] Patent Number: 5,474,929
[45] Date of Patent: Dec. 12, 1995

[54] SELECTABLE/REPORTER GENE FOR USE DURING GENETIC ENGINEERING OF PLANTS AND PLANT CELLS

[75] Inventor: Lawrence E. Pelcher, Saskatoon, Canada

[73] Assignee: National Research Council of Canada, Ottawa, Canada

[21] Appl. No.: 148,604

[22] Filed: Oct. 28, 1993

[51] Int. Cl.$^6$ .............................. A01H 1/04; C12N 5/14; C12N 15/00

[52] U.S. Cl. ................ 435/240.4; 435/69.1; 435/320.1; 435/172.3; 435/252.3

[58] Field of Search .......................... 435/240.4, 172.3, 435/69.1, 320.1, 252.3; 935/52, 55, 66, 67

[56] References Cited

U.S. PATENT DOCUMENTS

| | | | |
|---|---|---|---|
| 4,822,736 | 4/1989 | Kellems et al. | 435/91 |
| 5,073,675 | 5/1989 | Jones et al. | 800/205 |
| 5,166,059 | 11/1992 | Pastan et al. | 435/69.7 |

OTHER PUBLICATIONS

Kellems et al; "Adenosine Deaminase: A Dominant Amplifiable Genetic Marker For Use in Mammalian Cells" Gen. and Mol. Biol. of Ind. Micro. 1989 pp. 215–225.

Yeung et al: "Identification of Functional Murine Adenosine . . . " The Journal of Biological Chemistry—1985 vol. 260, No. 18 pp. 10299–10307.

van Beusechem et al; Proc. Natl. Acad. Sci. USA, vol. 89, pp. 7640–7644 Aug. 92 "Long–term expression of human adenosine deaminase . . . ".

Shen et al; Gene, 98 (1991) 283–287 "Construction and expression of an adenosine deaminase::lacZ fusion gene".

Yabuki et al; Biochimica et Biophysica acta, 1073 (1991) 474–480 "Catabolism of adenine nucleotides in suspension–cultured plant cell".

Butters et al; Physiological Plant Pathology (1985) 27 pp. 65–74 "Purine Metabolism in barley powdery mildew and its host".

Kaufman et al (1986) Proc Natl Acad Sci, USA 83: 3136–3140.

Primary Examiner—David T. Fox
Assistant Examiner—Elizabeth F. McElwain

[57] ABSTRACT

Adenosine deaminase gene (ADA gene) is used as a selectable/reporter gene for plant cells and plants. When introduced into plant cells, the ADA gene makes the cells resistant to inhibition by 2-deoxyadenosine or an analog, so transformed cells can be separated from non-transformed cells by culturing a cell mixture in a medium containing 2-deoxyadenosine or an analog in amounts that inhibit normal plant cells. A single vector may be constructed containing an ADA gene from any source (e.g. a mouse ADA gene) and an additional gene-of-interest to be introduced into plant cells. The vector may then be introduced into the cells by such a route as Agrobacterium infection or microprojectile bombardment. The presence of the ADA gene in successfully transformed plant cells may be confirmed by cultivating the cells in a medium containing 2-deoxyadenosine or an analog in the presence of a material that changes color in the presence of ammonia. Observation of a color change confirms the presence of the gene. DNA constructs containing both ADA genes and foreign genes-of-interest may be constructed, e.g. plasmid pRD360-ADA (ATCC 69459).

20 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1379 base pairs
( B ) TYPE: nucleic acid ( C ) STRANDEDNESS: single
( D ) TOPOLOGY: linear ( x i ) SEQUENCE DESCRIPTION: SEQ ID NO:1:

| CGACCCTGCC | AGCGAGCCAA | CGCAGACCCA | GAGAGCTTCG | GCGGAGAGAA | 50 |
| CCGGGAACAC | GCTCGGAACC | ATGGCCCAGA | CACCCGCATT | CAACAAACCC | 100 |
| AAAGTAGAGT | TACACGTCCA | CCTGGATGGA | GCCATCAAGC | CAGAAACCAT | 150 |
| CTTATACTTT | GGCAAGAAGA | GAGGCATCGC | CCTCCCGGCA | GATACAGTGG | 200 |
| AGGAGCTGCG | CAACATTATC | GGCATGGACA | AGCCCCTCTC | GCTCCCAGGC | 250 |
| TTCCTGGCCA | AGTTTGACTA | CTACATGCCT | GTGATTGCGG | GCTGCAGAGA | 300 |
| GGCCATCAAG | AGGATCGCCT | ACGAGTTTGT | GGAGATGAAG | GCAAAGGAGG | 350 |
| GCGTGGTCTA | TGTGGAAGTG | CGCTATAGCC | CACACCTGCT | GGCCAATTCC | 400 |
| AAGGTGGACC | CAATGCCCTG | GAACCAGACT | GAAGGGGACG | TCACCCCTGA | 450 |
| TGACGTTGTG | GATCTTGTGA | ACCAGGGCCT | GCAGGAGGGA | GAGCAAGCAT | 500 |
| TTGGCATCAA | GGTCCGGTCC | ATTCTGTGCT | GCATGCGCCA | CCAGCCCAGC | 550 |
| TGGTCCCTTG | AGGTGTTGGA | GCTGTGTAAG | AAGTACAATC | AGAAGACCGT | 600 |
| GGTGGCTATG | GACTTGGCTG | GGATGAGAC | CATTGAAGGA | AGTAGCCTCT | 650 |
| TCCCAGGCCA | CGTGGAAGCC | TATGAGGGCG | CAGTAAAGAA | TGGCATTCAT | 700 |
| CGGACCGTCC | ACGCTGGCGA | GGTGGGCTCT | CCTGAGGTTG | TGCGTGAGGC | 750 |
| TGTGGACATC | CTCAAGACAG | AGAGGGTGGG | ACATGGTTAT | CACACCATCG | 800 |
| AGGATGAAGC | TCTCTACAAC | AGACTACTGA | AAGAAACAT | GCACTTTGAG | 850 |
| GTCTGCCCCT | GGTCCAGCTA | CCTCACAGGC | GCCTGGGATC | CCAAAACGAC | 900 |
| GCATGCGGTT | GTTCGCTTCA | AGAATGATAA | GGCCAACTAC | TCACTCAACA | 950 |
| CAGACGACCC | CCTCATCTTC | AAGTCCACCC | TAGACACTGA | CTACCAGATG | 1000 |
| ACCAAGAAAG | ACATGGGCTT | CACTGAGGAG | GAGTTCAAGC | GACTGAACAT | 1050 |
| CAACGCAGCG | AAGTCAAGCT | TCCTCCCAGA | GGAAGAGAAG | AAGGAACTTC | 1100 |
| TGGAACGGCT | CTACAGAGAA | TACCAATAGC | CACCACAGAC | TGACGGGCGG | 1150 |
| GTCCCCTGAA | GATGGCAAGG | CCACTTCTCT | GAGCCTCATC | CTGTGGATAA | 1200 |
| AGTCTTTACA | ACTCTGACAT | ATTGACCTTC | ATTCCTTCCA | GACCTTGGAG | 1250 |
| AGGCCAGGTC | TGTCCTCTGA | TTGGATATCC | TGGCTAGGTC | CCAGGGGACT | 1300 |
| TGACAATCAT | GCACATGAAT | TGAAAACCTT | CCTTCTAAAG | CTAAAATTAT | 1350 |
| GGTGTTCAAT | AAAGCAGCTG | GTGACTGGT | | | 1379 |

( 2 ) INFORMATION FOR SEQ ID NO:2:

( i ) SEQUENCE CHARACTERISTICS:
( A ) LENGTH: 1156 base pairs
( B ) TYPE: nucleic acid
( C ) STRANDEDNESS: single
( D ) TOPOLOGY: linear ( x i ) SEQUENCE DESCRIPTION: SEQ ID NO:2:

| ATGGCCCAGA | CACCCGCATT | CAACAAACCC | AAAGTAGAGT | TACACGTCCA | 50 |
| CCTGGATGGA | GCCATCAAGC | CAGAAACCAT | CTTATACTTT | GGCAAGAAGA | 100 |
| GAGGCATCGC | CCTCCCGGCA | GATACAGTGG | AGGAGCTGCG | CAACATTATC | 150 |
| GGCATGGACA | AGCCCCTCTC | GCTCCCAGGC | TTCCTGGCCA | AGTTTGACTA | 200 |

```
CTACATGCCT  GTGATTGCGG  GCTGCAGAGA  GGCCATCAAG  AGGATCGCCT  250

ACGAGTTTGT  GGAGATGAAG  GCAAAGGAGG  GCGTGGTCTA  TGTGGAAGTG  300

CGCTATAGCC  CACACCTGCT  GGCCAATTCC  AAGGTGGACC  CAATGCCTG   350

GAACCAGACT  GAAGGGGACG  TCACCCCTGA  TGACGTTGTG  GATCTTGTGA  400

ACCAGGGCCT  GCAGGAGGGA  GAGCAAGCAT  TTGGCATCAA  GGTCCGGTCC  450

ATTCTGTGCT  GCATGCGCCA  CCAGCCCAGC  TGGTCCCTTG  AGGTGTTGGA  500

GCTGTGTAAG  AAGTACAATC  AGAAGACCGT  TCCCAGGCCA  CGTGGAAGCC  550

TATGAGGGCG  CAGTAAAGAA  TGGCATTCAT  CGGACCGTCC  ACGCTGGCGA  600

GGTGGGCTCT  CCTGAGGTTG  TGCGTGAGGC  TGTGGACATC  CTCAAGACAG  650

AGAGGGTGGG  ACATGGTTAT  CACACCATCG  AGGATGAAGC  TCTCTACAAC  700

AGACTACTGA  AAGAAACAT   GCACTTTGAG  GTCTGCCCCT  GGTCCAGCTA  750

CCTCACAGGC  GCCTGGGATC  CCAAAACGAC  GCATGCGGTT  GTTCGCTTCA  800

AGAATGATAA  GGCCAACTAC  TCACTCAACA  CAGACGACCC  CCTCATCTTC  850

AAGTCCACCC  TAGACACTGA  CTACCAGATG  ACCAAGAAAG  ACATGGGCTT  900

CACTGAGGAG  GAGTTCAAGC  GACTGAACAT  CAACGCAGCG  AAGTCAAGCT  950

TCCTCCCAGA  GGAAGAGAAG  AAGGAACTTC  TGGAACGGCT  CTACAGAGAA  1000

TACCAATAGC  CACCACAGAC  TGACGGGCGG  GTCCCCTGAA  GATGGCAAGG  1050

CCACTTCTCT  GAGCCTCATC  CTGTGGATAA  AGTCTTTACA  ACTCTGACAT  1100

ATTGACCTTC  ATTCCTTCCA  GACCTTGGAG  AGGCCAGGTC  TGTCCTCTGA  1150

TTGGAT                                                      1156
```

(2) INFORMATION FOR SEQ ID NO:3:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:3:

ATGGCCCAGA CACC     14

(2) INFORMATION FOR SEQ ID NO:4:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:4:

CTATTGGTAT TCTCTGTAGA GC     22

SELECTABLE/REPORTER GENE FOR USE DURING GENETIC ENGINEERING OF PLANTS AND PLANT CELLS

BACKGROUND OF THE INVENTION

I. Field of the Invention

This invention relates to selectable and reporter genes (sometimes referred to as dominant selectable marker genes) for use during the genetic engineering of plant cells to permit selection, detection and analysis of transformed plant cells and plants. More particularly, the invention relates to such genes, plasmids and vectors containing such genes, procedures for selecting transformed cells and plants containing such genes and procedures for detecting the presence of such genes in transformed plants.

II. Description of the Prior Art

Currently there are very few genes available for use during the genetic engineering of plants that can be used effectively for the selection, detection and analysis of transformed plants and plant cells (Walden et. al, *Methods in Molecular and Cellular Biology* 1: 175–194, 1990; the disclosure of which is incorporated herein by reference). This is an impediment to rapid and effective manipulation of genetic material in plants and makes the application of this technology more difficult than for other types of cells and organisms, i.e. animal cells, insect cells, microorganisms, and the like.

Most of the genes which are currently available for use in the selection of transformed plants or plant cells are either antibiotic- or herbicide-resistant genes, which tend to vary in their effectiveness in different plant species or to adversely interfere with the plant regeneration process. Additionally, the products of such genes are, in many cases, enzymes which cannot easily be detected or asseyed (Jefferson, *Genetic Engineering: Principles and Methods* 10: 247–263, 1988 Palenum Press).

Accordingly, the lack of effective single, selectable/reporter genes applicable to the plant kingdom has made it necessary to develop complex multigene transformation systems based on selectable antibiotic or herbicide resistance genes used in combination with other reporter genes, the products of which can be detected or assayed.

Currently, there are three general approaches used for providing selectability and detectability during genetic transformation of plants. In a first approach, a single, selectable gene, conferring antibiotic or herbicide resistance, is introduced to plant cells at the time of transformation. The gene confers resistance to a selecting agent, such as the antibiotic neomycin (Herrera-Estrella et. al., *European Molecular Biology Organization Journal* <hereinafter "EMBO J."> 2: 987–995, 1983) or the herbicide phosphinothricin (DeBlock et.al., *EMBO J.* 6: 2513–2518, 1987).

Shortly after transformation, cells are exposed to the selection agent which kills nontransformed cells. In some applications, the products of these genes are not easily assayed (Reiss et. al., *Gene* 30: 211–218, 1984).

In a second approach, two separate genes are introduced into plant cells at the time of transformation. One of the genes is a selectable gene, e.g. the gene expressing neomycin phosphotransferase-II (NPT-II), used to confer resistance to selection agents, such as the antibiotic kanamycin (Herrera-Estretta et. al., supra). The other of the genes is a reporter gene, e.g. β-glucuronidase (GUS) gene. This enzyme is relatively easy to assay for and produces an indigo colored product when incubated with the 5-bromo-4-chloro-3-indolyl glucuronidase [XGluc] (Jefferson et. al., *EMBO J.* 6: 3201–3207, 1987).

In the third approach, two separate genes such as NPT-II and GUS are fused together to produce a single bifunctional gene product referred to as a fusion gene (NPT-II/GUS), which confers resistance to a selection agent such as kanamycin and also confers the ability to produce a characteristic color reaction when incubated with XGluc (Datla et al., *Gene* 101: 239–246, 1991).

Unfortunately, the use of either multigene or fusion gene systems which depend on antibiotic resistance or herbicide resistance as the selectable component has raised concerns regarding potential undesirable effects in the agricultural industry and on environmental grounds (Gressel, *TIBTECH* 10: 382, 1992; Bryant & Leather, *TIBTECH* 10: 274–275, 1992; and Flavell et. al., *Bio/Technology* 10: 141–144, 1992).

There is therefore a need for an improved system allowing for the selection, detection and analysis of transformed plant cells.

SUMMARY OF INVENTION

It is an object of the present invention to enable plant cells and plants transformed by genetic engineering to be selected, detected and analyzed in a relatively simple and reliable fashion.

Another object of the invention is to provide a single selectable/reporter gene suitable for introduction and use in various plant systems.

Another object of the invention is to enable the selection, detection and analysis of plant cells and plants without having to rely on genes that confer antibiotic or herbicidal resistance to transformed cells.

Other objects, advantages and features of the invention will be apparent from the following description.

According to one aspect of the present invention, there is provided a genetically transformed plant cell containing a foreign gene or gene portion expressing an adenosine deaminase enzyme.

According to another aspect of the invention, there is provided a process of genetic transformation of plant cells, comprising: preparing plant cells for transformation; exposing said plant cells to a vector for introducing foreign DNA into the genome of the cell to form a mixture of cells comprising successfully transformed cells and other cells; selecting said successfully transformed plant cells; and amplifying said successfully transformed plant cells; wherein said vector contains a gene or gene portion expressing an adenosine deaminase enzyme and said successfully transformed plant cells are selected by culturing said cell mixture in the presence of deoxyadenosine or an analog thereof at a concentration that inhibits normal plant cells, and selecting plant cells that are not substantially inhibited.

According to yet another object of the invention, there is provided a process as indicated above further comprising determining the presence of said gene or gene portion in said selected cells by incubating said selected cells or extracts thereof, in the presence of adenosine, deoxyadenosine or an analog thereof and a compound that changes color in the presence of ammonia, and observing a change of color of the incubation medium confirming the presence of said gene or gene portion in said selected cells.

The present invention makes it possible to introduce a single gene into plant cells at the time of transformation and to use that gene to effect selection of the successfully transformed cells without the need to introduce antibiotic or herbicide resistance into the transformed cells.

The invention also provides a simple colorimetric method for detecting the transformed cells without resorting to the introduction of multiple or fused genes.

DETAILED DESCRIPTION OF THE INVENTION

Figure 1:
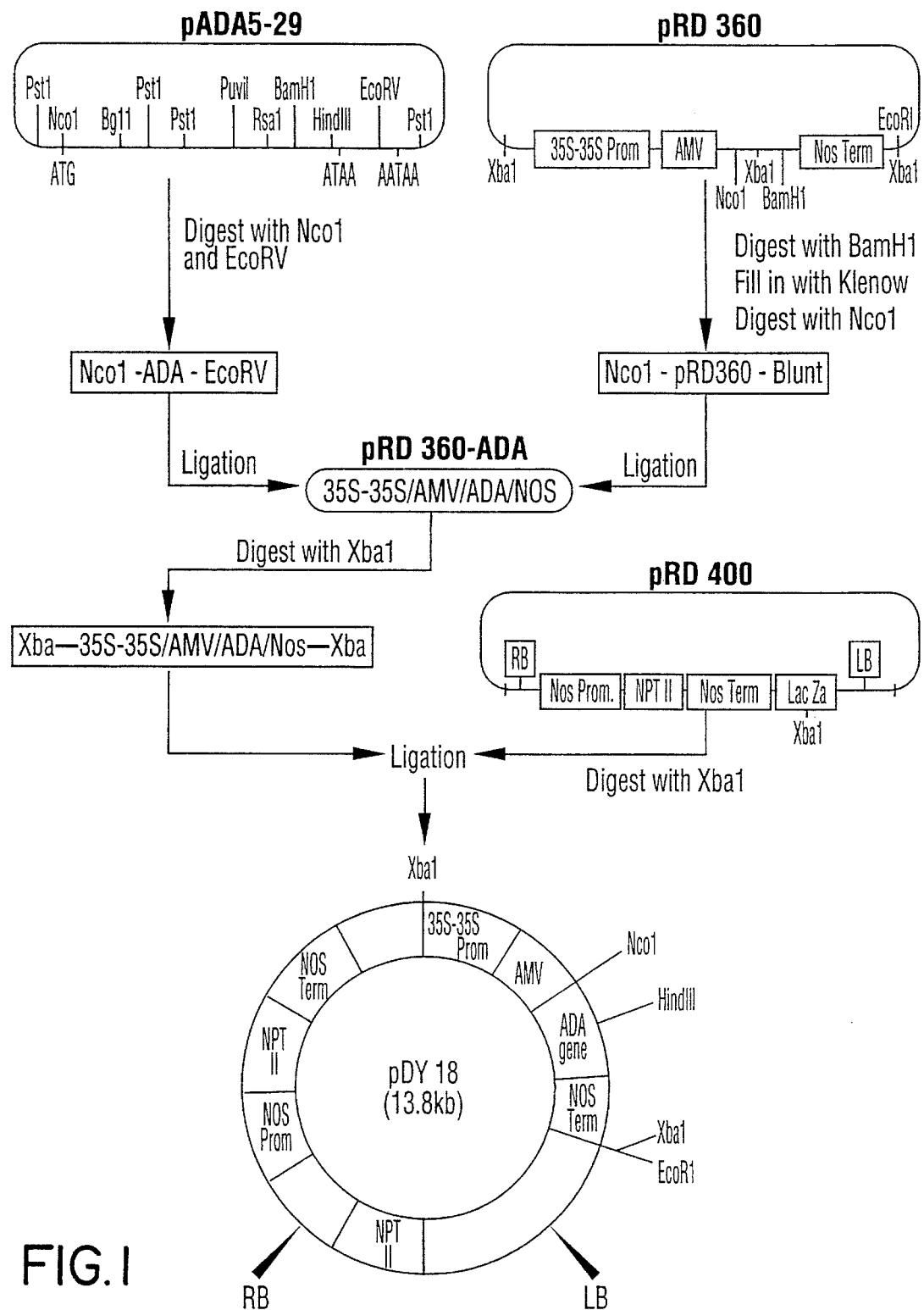
FIG. 1 is a diagram of a plasmid containing a gene expressing ADA and steps in a method of manipulating said gene for introduction into a plant vector.

Stated broadly, the present invention relates to the use of an adenosine deaminase gene as a selectable/reporter gene in plant cells to facilitate the selection and analysis of plant cells containing other genes-of-interest co-introduced into the cells at the time of transformation.

It has been found that the growth of plant cells, such as soybean (SB-1), tobacco and Brassica sp., among others, is inhibited by the presence in the culture medium of deoxyadenosine and its analogs, e.g. 2-deoxyadenosine, cordycepin (3-deoxyadenosine), ara-A (9-B-D-arabinofuranosyl adenine), xyl-A (9-B-D-xylofuranosyl adenine), 2,6-diaminopurine riboside, 6-chloropurine riboside, 6-methoxypurine riboside, and 2'-3'-dideoxyadenosine and 2-chloroadenosine. Consistent with the above observations are the reported absence of detectable ADA in barley leaves (Butters et. al., *Physio. Plant Path.* 27: 65–74, 1985) and cell cultures of periwinkle (Yabuki, N. and Ashihara, H., *Biochimia et Biophysica Acta* 1073: 474–480, 1991). These observations indicate to the inventor of the present invention either that the ADA gene is absent in multicellular plants or is expressed only under tight developmental control. To overcome this observed broadly-based deficiency of plant cells, ADA genes flanked by the appropriate plant regulatory elements are, according to the present invention, introduced into plant transformation vectors and thus into the genomes of plant cells. The vector may be introduced into plant cells by any suitable technique, e.g. Agrobacterium mediated transformation or micro-projectile bombardment (so-called biolistic) mediated transformation where the vector under consideration is adsorbed onto inert particles and shot into plant cells (cf. V. Vasil, et al, Bio/Technology, 9: 743–747, 1991; the disclosure of which is incorporated herein by reference).

The transformed cells produced in this way can then be separated from non-transformed or unsuccessfully-transformed cells by culturing the cells in a medium containing deoxyadenosine or one of its analogs as a selecting agent. Cells containing the ADA-producing gene are not inhibited by the selecting agent, whereas the nontransformed cells are inhibited or killed. The ADA gene can thus be used as a selectable gene for genetically transformed plants.

It will be apparent from the above that the criterion for applicability of the present invention to a particular plant is the inability of cells of the plant to grow in the presence of deoxyadenosine or an analog thereof.

It has been known for some time that deoxyadenosine is inhibitory to mammalian cells in culture and that inborn genetic defects in adenosine metabolism in man are related to a deficiency in ADA (Giblette et. al., Lancet 2: 1067–1069, 1972). Further, it has also been demonstrated that increased sensitivity to deoxyadenosine and its analogs can be correlated with decreases in ADA activity (Fox and Kelly, *Ann. Rev. Biochem.* 47: 655–686, 1978). Moreover, adenosine deaminase has been suggested for use as a selectable genetic marker in mammalian cells (Kellems, et al., *Genet. and Mol. of Indust. Microorg.*: 216–225, 1989; the disclosure of which is incorporated herein by reference). However, there has been no previous suggestion or demonstration that ADA-producing genes can be used as selectable/reporter genes in plant cells or plants.

While the effectiveness of ADA-producing genes as selectable genes for plant cells and plants is extremely useful, it has also been found by the inventor of the present invention that adenosine deaminase produced in ADA-transformed plant cells can be detected by colorimetric tests, whereas adenosine deaminase is not detected in non-transformed cells or protein enriched extracts from such cells. This demonstrates that such colorimetric tests can be used to indicate the presence of transformed cells. Still further, it has been found that colorimetric assays may be used to determine quantities of ADA produced by transformed cells based on extrapolation against a standard curve obtained using commercially available adenosine deaminase (Guisti and Galanti, *Methods of Enzymatic Analysis* Vol. IV 317–323, Verlag Chemie; the disclosure of which is incorporated herein by reference). In the Guisti and Golanti method, the ammonia can be determined directly or indirectly by detecting an increase in pH brought about by the ammonia generation. Various pH indicators, such as phenol red and bromthymol blue, can be used to detect pH increases via color change in their sensitive range between pH 5 and pH 7 and therefore can be used to directly assay for ADA activity in extracts from reputed transformed tissues. The use of indicators alone cannot quantify the ammonia formation, but quantification can be estimated by comparison with standard curves, as indicated above.

Quantification is of interest for the following reasons. Firstly, the site of integration of the foreign gene into the plant cell genome appears to be random and can affect the level of expression of the foreign gene. Secondly, more than one copy of the gene may be integrated into the genome, which also can affect the level of expression of the foreign gene. It is of value to be able to analyze transformed cells or plants to screen for desirable expression levels. In transforms produced by the present invention, the ADA gene used as a selectable/reporter gene is closely associated with the gene-of-interest in the vector construct. Therefore the expression of the ADA gene is likely to reflect accurately the expression of the gene of interest.

That such colorimetric assays can be used to quantify ADA expression in transformed plant cells is unexpected as it is not used to detect activity in transformed mammalian cells. This is evident from a paper by van Beusechem et. al. *Proc Natl. Acad. Sci.* U.S.A., 89: 7640–7644, 1992, where human ADA was detected by zymogram analysis, and can also be seen from a recent report of the construction of a fusion gene for mammalian cells using an ADA gene and the bacterial β-galactosidase gene to enable colorimetric detection of cells containing the ADA gene (Shen et al., *Gene* 98: 283–287,1991).

Thus, ADA-producing genes can be used as effective single selectable/reporter genes for introduction into plant genomes at the same time as other foreign genetic material (one or more gene-of-interest). Suitable ADA-producing genes may be obtained from different sources, e.g. mammals such as humans, mice, etc., or other organisms such as bacteria (e.g. E. coli) and yeasts. Such genes are available from samples in cDNA libraries or can be extracted specifically for the present invention. By definition, ADA genes from all sources are capable of producing adenosine deaminase and are thus useful in the present invention regardless of the source. Moreover, all such genes can be excised and incorporated into suitable vectors in similar ways that will be apparent to persons skilled in the art after reading the disclosure of the present application.

Vectors containing ADA genes can be used successfully to introduce a second foreign gene (gene-of-interest) into transformed plant cells and plants. The gene-of-interest may be inserted into a multiple restriction enzyme cloning (MCS) site or any other suitable restriction site of the vector containing the ADA gene. For example, as explained in much greater detail in the Examples below, an ADA gene-containing vector has been used to co-introduce and express neomycin phosphotransferase II (NPT II) in plant cells. After transformation and selection with a deoxyadenosine analog containing medium (cordycepin or ara-A) regenerated shoots were able to grow on culture medium containing kanamycin, which inhibits the growth on non-transformed tissues. It will be clear to persons skilled in the art that other genes-of-interest may be co-introduced in essentially the same way. Large numbers of potential genes-of-interest for plant cells are available from DNA libraries and researchers in this field, and additional ones are being discovered all of the time. A large number of examples of potential genes-of-interest could be provided, but different genes will clearly be of interest to different researchers at different times and the identity of such genes is not critical to the present invention. Indeed, an advantage of the present invention is that it is suitable for introduction of a large variety of genes-of-interest and can thus be adopted as a common procedure for facilitating the manipulation of plant genomes.

In the following description, reference is made to the scheme shown in accompanying FIG. 1 as an illustration of one way in which an ADA gene and a gene-of-interest can be introduced into a suitable vector. Experimental details of this procedure are provided later in the Examples.

The ADA Gene

A gene expressing ADA has been cloned from a mouse cell line (Yeung et al., *J. Biol. Chem.* 260: 10299–10307, 1985; the disclosure of which is incorporated herein by reference). The gene isolated in this way is available in the form of a plasmid (pADA5-29) deposited at and available from The American Type Culture Collection, 12301 Parklawn Drive, Rockville, Md. 20852, U.S.A. under deposit number ATCC 63062. As will be explained more fully below, plasmids of this type can be used to create plant transformation vectors for the introduction of the ADA gene, and at the same time other foreign genetic material, into plant cells.

The gene sequence [SEQ ID NO:1] reported by Yeung et al is shown as follows:

| | | | | | |
|---|---|---|---|---|---|
| CGACCCTGCC | AGCGAGCCAA | CGCAGACCCA | GAGAGCTTCG | GCGGAGAGAA | 50 |
| CCGGGAACAC | GCTCGGAACC | ATGGCCCAGA | CACCCGCATT | CAACAAACCC | 100 |
| AAAGTAGAGT | TACACGTCCA | CCTGGATGGA | GCCATCAAGC | CAGAAACCAT | 150 |
| CTTATACTTT | GGCAAGAAGA | GAGGCATCGC | CCTCCCGGCA | GATACAGTGG | 200 |
| AGGAGCTGCG | CAACATTATC | GGCATGGACA | AGCCCCTCTC | GCTCCCAGGC | 250 |
| TTCCTGGCCA | AGTTTGACTA | CTACATGCCT | GTGATTGCGG | GCTGCAGAGA | 300 |
| GGCCATCAAG | AGGATCGCCT | ACGAGTTTGT | GGAGATGAAG | GCAAAGGAGG | 350 |
| GCGTGGTCTA | TGTGGAAGTG | CGCTATAGCC | CACACCTGCT | GGCCAATTCC | 400 |
| AAGGTGGACC | CAATGCCCTG | GAACCAGACT | GAAGGGGACG | TCACCCCTGA | 450 |
| TGACGTTGTG | GATCTTGTGA | ACCAGGGCCT | GCAGGAGGGA | GAGCAAGCAT | 500 |
| TTGGCATCAA | GGTCCGGTCC | ATTCTGTGCT | GCATGCGCCA | CCAGCCCAGC | 550 |
| TGGTCCCTTG | AGGTGTTGGA | GCTGTGTAAG | AAGTACAATC | AGAAGACCGT | 600 |
| GGTGGCTATG | GACTTGGCTG | GGGATGAGAC | CATTGAAGGA | AGTAGCCTCT | 650 |
| TCCCAGGCCA | CGTGGAAGCC | TATGAGGGCG | CAGTAAAGAA | TGGCATTCAT | 700 |
| CGGACCGTCC | ACGCTGGCGA | GGTGGGCTCT | CCTGAGGTTG | TGCGTGAGGC | 750 |
| TGTGGACATC | CTCAAGACAG | AGAGGGTGGG | ACATGGTTAT | CACACCATCG | 800 |
| AGGATGAAGC | TCTCTACAAC | AGACTACTGA | AAGAAAACAT | GCACTTTGAG | 850 |
| GTCTGCCCCT | GGTCCAGCTA | CCTCACAGGC | GCCTGGGATC | CCAAAACGAC | 900 |
| GCATGCGGTT | GTTCGCTTCA | AGAATGATAA | GGCCAACTAC | TCACTCAACA | 950 |
| CAGACGACCC | CCTCATCTTC | AAGTCCACCC | TAGACACTGA | CTACCAGATG | 1000 |
| ACCAAGAAAG | ACATGGGCTT | CACTGAGGAG | GAGTTCAAGC | GACTGAACAT | 1050 |
| CAACGCAGCG | AAGTCAAGCT | TCCTCCCAGA | GGAAGAGAAG | AAGGAACTTC | 1100 |
| TGGAACGGCT | CTACAGAGAA | TACCAATAGC | CACCACAGAC | TGACGGGCGG | 1150 |
| GTCCCCTGAA | GATGGCAAGG | CCACTTCTCT | GAGCCTCATC | CTGTGGATAA | 1200 |
| AGTCTTTACA | ACTCTGACAT | ATTGACCTTC | ATTCCTTCCA | GACCTTGGAG | 1250 |
| AGGCCAGGTC | TGTCCTCTGA | TTGGATATCC | TGGCTAGGTC | CCAGGGGACT | 1300 |
| TGACAATCAT | GCACATGAAT | TGAAAACCTT | CCTTCTAAAG | CTAAAATTAT | 1350 |
| GGTGTTCAAT | AAAGCAGCTG | GTGACTGGT. | | | |

The following section of this sequence (nucleotides 71–1276) [SEQ ID NO:2], released by cutting with restriction enzymes Nco1 and EcoRV, has been used in the manner explained below to construct an exemplary vector in the present invention:

| | | | | | | |
|---|---|---|---|---|---|---|
| ATGGCCCAGA | CACCCGCATT | CAACAAACCC | AAAGTAGAGT | TACACGTCCA | | 50 |
| CCTGGATGGA | GCCATCAAGC | CAGAAACCAT | CTTATACTTT | GGCAAGAAGA | | 100 |
| GAGGCATCGC | CCTCCCGGCA | GATACAGTGG | AGGAGCTGCG | CAACATTATC | | 150 |
| GGCATGGACA | AGCCCCTCTC | GCTCCCAGGC | TTCCTGGCCA | AGTTTGACTA | | 200 |
| CTACATGCCT | GTGATTGCGG | GCTGCAGAGA | GGCCATCAAG | AGGATCGCCT | | 250 |
| ACGAGTTTGT | GGAGATGAAG | GCAAAGGAGG | GCGTGGTCTA | TGTGGAAGTG | | 300 |
| CGCTATAGCC | CACACCTGCT | GGCCAATTCC | AAGGTGGACC | CAATGCCCTG | | 350 |
| GAACCAGACT | GAAGGGGACG | TCACCCCTGA | TGACGTTGTG | GATCTTGTGA | | 400 |
| ACCAGGGCCT | GCAGGAGGGA | GAGCAAGCAT | TTGGCATCAA | GGTCCGGTCC | | 450 |
| ATTCTGTGCT | GCATGCGCCA | CCAGCCCAGC | TGGTCCCTTG | AGGTGTTGGA | | 500 |
| GCTGTGTAAG | AAGTACAATC | AGAAGACCGT | TCCCAGGCCA | CGTGGAAGCC | | 550 |
| TATGAGGGCG | CAGTAAAGAA | TGGCATTCAT | CGGACCGTCC | ACGCTGGCGA | | 600 |
| GGTGGGCTCT | CCTGAGGTTG | TGCGTGAGGC | TGTGGACATC | CTCAAGACAG | | 650 |
| AGAGGGTGGG | ACATGGTTAT | CACACCATCG | AGGATGAAGC | TCTCTACAAC | | 700 |
| AGACTACTGA | AAGAAAACAT | GCACTTTGAG | GTCTGCCCCT | GGTCCAGCTA | | 750 |
| CCTCACAGGC | GCCTGGGATC | CCAAAACGAC | GCATGCGGTT | GTTCGCTTCA | | 800 |
| AGAATGATAA | GGCCAACTAC | TCACTCAACA | CAGACGACCC | CCTCATCTTC | | 850 |
| AAGTCCACCC | TAGACACTGA | CTACCAGATG | ACCAAGAAAG | ACATGGGCTT | | 900 |
| CACTGAGGAG | GAGTTCAAGC | GACTGAACAT | CAACGCAGCG | AAGTCAAGCT | | 950 |
| TCCTCCCAGA | GGAAGAGAAG | AAGGAACTTC | TGGAACGGCT | CTACAGAGA | | 1000 |
| TACCAATAGC | CACCACAGAC | TGACGGGCGG | GTCCCCTGAA | GATGGCAAGG | | 1050 |
| CCACTTCTCT | GAGCCTCATC | CTGTGGATAA | AGTCTTTACA | ACTCTGACAT | | 1100 |
| ATTGACCTTC | ATTCCTTCCA | GACCTTGGAG | AGGCCAGGTC | TGTCCTCTGA | | 1150 |
| TTGGAT. | | | | | | |

Construction of Plasmids and Plant Transformation Vectors containing the Adenosine Deaminase Gene and *Agrobacterium tumefaciens* Harboring these Vectors Using standard techniques as mentioned above, the ADA gene [SEQ ID NO:2] can be released from the cloned sequence, inserted into a suitable cassette plasmid containing plant regulatory sequences, amplified and the ADA cassette isolated therefrom and introduced into a suitable binary plant vector for conjugative transfer into a suitable plant gene vector, for example *Agrobacterium tumefaciens* or *Agrobacterium rhizogenes*.

The ADA gene can be removed from the original plasmid by digestion with restriction endonucleases which cut immediately flanking the coding sequence of the gene but which do not cut within the gene. In the case of the mouse ADA gene enzyme in the plasmid pADA5-29, Nco1 and EcoRV may be used as shown in FIG. 1. The purified gene can then be inserted into the multiple restriction enzyme cloning site (MCS) or polylinker site of an intermediate plasmid or vector (e.g. pRD360 shown in FIG. 1, sometimes referred to as a cassette plasmid to form a new vector containing the ADA gene (e.g. plasmid pRD360-ADA shown in FIG. 1, which has been deposited at the American Type Culture Collection under the terms of the Budapest Treaty, accession number ATCC 69459). Such plasmids contain MCS flanked by plant regulatory sequences which enhance expression of foreign genes in transformed plant cells and plants (Walden et. al., supra). Such sequence elements preceding the gene are referred to as promoters (prom. i.e. CaMV 35S.) and ribosome binding sites (rbs. i.e. AMV), which may or may not overlap, but interact to direct the correct qualitative and quantitative gene expression. Following the gene are termination signals (term. i.e. nopaline synthase terminator) which assure correct termination of the protein and polyadenylation of messenger RNA transcribed from the foreign gene. The resulting complete cassette (promoter-rbs-ADA-terminator) can be removed from pRD 360-ADA by cutting with the appropriate restriction enzyme (Xba1 in FIG. 1), purified and ligated into the MCS of an Agrobacterium binary vector (i.e. pBIN 19, pBI101, pBI121, pRD400 (Bevan, *Nucl. Acid Res.*, 12: 8711–8721, 1984; Jefferson, *EMBO J.* 6: 3901–3907, 1987; and Datla et. al., *Gene* 211: 383–384, 1992; the disclosures of which are incorporated herein by reference), pRD400 being shown in FIG. 1. Such binary vectors contain origins of replication which enable replication in *E. coli* and Agrobacterium, an antibiotic resistance gene for selection in both bacteria, boarder repeats which define the DNA to be transferred to the plant genome and a MCS flanked by the repeat boarders. The binary vector pRD400 used in this example also contained the NPT II gene within the boarders constituting a foreign gene-of-interest to be introduced into a plant cell using the ADA gene as a selectable/reported gene. The NPT II gene can be replaced by standard techniques with an appropriate MCS for insertion of other genes of interest, as will be apparent to persons skilled in the art.

The resulting binary vectors (pDY18 in FIG. 1) can be conjugatively transferred from *E. coli* into *Agrobacterium tumefaciens* harboring a Ti plasmid by triparental mating (Fraley et. al., *Proc. Natl. Sci.* U.S.A. 80: 4803–4806, 1983; the disclosure of which is incorporated herein by reference) with *E. coli* harboring pRK2013 which facilitates the mobilization of the binary vector into Agrobacterium (Ditta et. al. *Proc. Natl. Sci.* U.S.A. 77: 7347–7351, 1980; the disclosure of which is incorporated herein by reference).

Introduction of ADA gene into plant cells

The ADA gene can be introduced into plant cells by co-cultivation of leaf tissues with *Agrobacterium tumefaciens* or other transformed species containing a disarmed (non-tumorgenic) helper Ti plasmid and a binary vector containing the ADA gene inserted as described above (Horsch et. al., *Science* 227: 1229–1231, 1985; the disclosure of which is incorporated herein by reference). The leaf tissues are generally briefly dipped in a solution containing the Agrobacterium, blotted dry and placed on a plant tissue culture medium for two days (Draper, *Plant Genetic Transformation and Gene Expression:* A Laboratory Manual, Blackwell Scientific Publs; the disclosure of which is incorporated herein by reference). It is during this time that the DNA flanked by the boarder repeats is transferred from the Agrobacterium to the genome of the plant cells (Buchanan-Wollaston, *Nature* 328: 172–175, 1987). The leaf tissue may then be transferred to medium containing an antibiotic which inhibits further growth of the Agrobacterium.

Selection of transformed plant cells and plants

Successfully transformed plant cells can be selected by transfer of the treated tissues to fresh shoot inducing tissue culture medium containing an antibiotic which inhibits further growth of Agrobacterium (e.g. carbenicillin) and deoxyadenosine or an analog at concentrations which inhibit the growth of non-transformed cells (i.e. 50 µM cordycepin or 100 µM ara-A). After 30–45 days in culture, the resistant shoots can be transferred to rooting medium which may contain deoxyadenosine or an analog thereof or other selective agent. Regenerated plants may then be transferred to soil for further growth, analysis and seed setting.

Colorimetric Determination and Analysis

The ADA gene can be made use of as a reporter gene in the following ways. In the presence of ADA, adenosine is converted to inosine and ammonia. Standard assays for the detection of ADA follow a decrease in optical density in the UV range at 265 nm as adenosine is converted to inosine (Lupidi et. al., *Biochemia et Biophysica Acta* 1122: 311–316, 1992; the disclosure of which is incorporated herein by reference). The present invention, in contrast, makes use of the evolution of ammonia to generate colored products which can be detected and measured.

A first approach is based on a colorimetric assay for ADA reported by Guisti and Galanti, (supra). In this assay, ammonia forms an intense blue indophenol with sodium hypochlorite and phenol in alkaline solution. Sodium nitroprusside is the catalyst in this reaction. The ammonia concentration is directly proportional to the blue indophenol produced.

To assay for the activity of ADA in leaf or callus tissues, small amounts of tissue may be incubated in a solution containing adenosine, deoxyadenosine or one of the analogs. Phenol/nitroprusside solution and alkaline hypochlorite solution are then added to the incubation mixture and incubation is continued for color development. The incubation medium containing tissues from transformed plants develops an intense blue color while medium containing tissues from non-transformed plants or tissues from plants transformed with a gene other than ADA remains colorless or only faintly light blue.

A second approach employs a pH (acid/alkali) indicator, e.g. the biological stains bromthymol blue or phenol red which in acid solution are clear or yellow and in alkaline solution blue or dark red, respectively. As ammonia is evolved during the conversion of adenosine or other analogs to inosine compounds, there is an increase in the pH of the incubation mixture. The increase in pH can easily be detected by the indicator. In this approach, plant tissue is incubated in a weakly buffered acidic solution of adenosine, deoxyadenosine or an analog and then a solution containing the indicator is added. A change in the color of the indicator shows the conversion of the deoxyadenosine or analog to deoxyinosine and ammonia and thus the presence of transformed tissue. In contrast, non-transformed tissue does not produce any change in the color or the indicator.

These two colorimetric assays enable the easy detection and analysis of ADA in transformed plant tissues.

Having explained the methods and procedures used in the present invention in general terms above, the invention is illustrated further by the following specific Examples, but is not limited thereto.

EXAMPLE 1

Inhibition of Plant Cell growth by Deoxyadenosine and its Analogs.

Table 1 below shows the results of observations on the inhibitory effects of increasing concentrations of 2'-deoxy-adenosine on the growth of soybean cells (*Glycine max*) line SB-1 grown on Gamborg's medium (B5, Sigma). Aliquots of cells were subcultured to medium containing either 0, 0.74 µM, 7.4 µM, 74 µM of 2'-deoxyadenosine and cultured for 6 days. The cells were then harvested on filters, oven dried and weighed. All three concentrations of 2'-deoxyadenosine proved to be inhibitory to the growth of soybean cells.

TABLE 1

Effects of 2'-deoxyadenosine on cell growth in culture

| 2'-deoxyadenosine concentration (µM) | Increase In Dry Weight* (mg) |
| --- | --- |
| 0 | 118.01 |
| 0.74 | 6.05 |
| 7.40 | 3.51 |
| 74.00 | 1.93 |

*Average dry weight increase after 6 days in culture.

To confirm the above results and to confirm that analogs of deoxyadenosine also inhibit plant cell growth, the effect of increasing concentrations of 2'-deoxyadenosine, ara-A and cordycepin (3'-deoxyadenosine) was studied using tobacco (*Nicotiana tabacum* cv. Xenthi) leaf explants grown on Murashige and Skoogs basal medium containing Gamborg's vitamins (MS/B5). The fresh weight increase was determined after 3 weeks in culture.

All three compounds proved to be inhibitory to the growth of the tobacco explants as shown in Table 2 below.

TABLE 2

Effects of adenosine, 2'-deoxyadenosine and arabinofuranosyl adenine and cordycepin on the growth of tobacco leaf explant

|  | COMC (µM) | Increase in Fresh Weight* (g) |
| --- | --- | --- |
| Adenosine | 40 | 0.95 + 0.069 |
|  | 80 | 0.81 + 0.060 |
|  | 160 | 0.94 + 0.056 |
|  | 320 | 0.57 + 0.052 |
| 2'-deoxyadenosine | 40 | 0.74 + 0.058 |
|  | 80 | 0.96 + 0.050 |
|  | 160 | 0.32 + 0.038 |
|  | 320 | 0.07 + 0.005 |
|  | 640 | 0.04 + 0.003 |
| Arabinofuranosyl | 5 | 0.56 + 0.047 |
|  | 10 | 0.32 + 0.037 |
|  | 20 | 0.23 + 0.025 |
|  | 40 | 0.10 + 0.048 |
|  | 80 | 0.05 + 0.008 |
|  | 160 | 0.02 + 0.001 |
| Cordycepin | 5 | 0.61 + 0.059 |
|  | 10 | 0.10 + 0.016 |
|  | 20 | 0.06 + 0.008 |
|  | 40 | 0.04 + 0.049 |
|  | 80 | 0.02 + 0.001 |
|  | 160 | 0.02 + 0.001 |
| Control | 0 | 0.55 + 0.065 |

*Average fresh weight increase after 3 weeks in culture.

EXAMPLE 2

Construction of Plant Transformation Vectors Containing the Adenosine Deaminase Gene and *Agrobacterium tumefaciens* MP90 Harboring These Vectors.

Referring again to FIG. 1, the adenosine deaminase (ADA) coding sequence [SEQ ID NO:2] was isolated from plasmid pADA5-29 by digesting 1 µg plasmid with restriction enzyme EcoRV (10 units) in a 20 µl reaction mixture containing 50 mM Tris-HCl (pH8.0), 10 mM MgCl$_2$, 50 mM NaCl, at 37° C. for 1 hour. The DNA was precipitated with 2.5 volumes ethanol and washed twice with 70% ethanol and dried. The plasmid DNA was then digested with Nco1 (10 units) in a 20 µl reaction mixture containing 50 mM Tris-HCl (pH8.0), 10 mM MgCl$_2$, 100 mM NaCl at 37° C. for 1–3 hours. The digested plasmid was then subjected to electrophoresis through 0.8% agarose and the 1.2 kilobase (Kb) DNA band containing the complete ADA coding sequence (base 1 to base 1207) [SEQ ID NO:2] was excised. The DNA (Nco1-ADA-EcoRV) was electroeluted, precipitated with 2 volumes ethanol, washed twice with 70% ethanol, dried and dissolved in distilled water.

One microgram of the cassette vector pRD360 (obtainable from the National Research Council of Canada (NRC), Plant Biotechnology Institute, Ottawa, Canada), which contains a MCS or PLS flanked by tandem CaMV 35S promoters and an AMV leader sequence on one side and a nopaline synthase terminator on the other, was cut within MCS with BamH1 (10 units) in a 20 µl reaction mixture containing 50 mM TrisHCl (pHS8.0), 10 mM MgCl$_2$, 100 mM NaCl at 37° C. for 1 hour. The linearized plasmid was precipitated, washed with ethanol, dried and dissolved in distilled water. The 5' protruding ends produced during the BamH1 linearization of the plasmid were filled in a 50 µl reaction mixture containing 2 units DNA polymerize Klenow Fragment, 50mM Tris-HCl (pH8.0), 4 mM MgCl$_2$, 5 mM DTT, 50 µg/ml BSA, 0.1 mM dNTPs (dATP, dCTP, dGTP, dTTP) at 37° C. for 1 hr.

The reaction was stopped by heating to 80° C. for 15 minutes. The DNA was precipitated, washed with ethanol, dried and dissolved in distilled water. The linearized plasmid (3.8 Kb) was then cut within the MCS with Nco1 as described above. This procedure yielded a linearized plasmid with one end being an Nco1 overhang and the other end being a blunt end exactly complementary to the ends of the ADA gene isolated as described above.

The DNA fragments Nco1-ADA-EcoRV and Nco1-pRD360-Blunt (1:2 ratio) were ligated together in a 20 µl reaction mixture containing approximately 200 ng DNA, 0.1 unit T4 DNA ligase, 50 mM Tris-HCl (pH 7.6), 10 mM MgCl$_2$, 1 mM ATP, 1 mM DTT, 5% polyethylene glycol-8000 at 4°–12° C. overnight.

Approximately 2.5 µl of the ligation mixture containing pRD360-ADA was used to transform 100 µl competent E. coli DH5α cells. The mixture was held on ice for 1 hr, heated to 42° C. for 90 seconds and cooled on ice for 2 min. The cells were incubated at 35° C. for 90 min. following the addition of 400 µl Luria(L) broth.

One hundred µl of the culture spread on L broth agar containing 50 µg/ml ampicillin and incubated at 37° C. overnight. Colonies were selected, grown in L broth containing 25 µg/ml ampicillin and the plasmid (pRD360-ADA) DNA isolated by the alkaline lysis method (Maniatis et. el. *Molecular Cloning*, 1982, Cold Spring Harbor Publs.; the disclosure of which is incorporated herein by reference).

The plasmid (pRD360-ADA) was digested with Xba1 in a 20 µl reaction mixture containing 50 mM Tris-HCl pH8.0, 10 mM MgCl$_2$, 50 mM NaCl at 37° C. for 1 hr. The plasmid digest was subjected to 0.8% agarose gel electrophoresis and the 2.2 Kb fragment (Xba-35S-35S-AMV-ADA-Nos term.-Xba) as shown in FIG. 1 was isolated as described above. This fragment was ligated into plasmid pRD400 (Dr. Raju Datla, National Research Council of Canada/Plant Biotechnology Institute, Ottawa, Canada) and linearized with Xba1 as described above. The resulting plasmid pDY18, was transformed into competent E. coli DH5α and the transformants, E. coli DH5α/pDY18, were selected after growth on L agar containing 25 µg/ml kanamycin and used in the triparental mating with A. tumefaciens (MP90) described below.

Plasmid pDY18 was conjugatively transferred from E. coli DH5α to A. tumefaciens (MP90) by triparental mating as follows; bacterial cells E. coli DH5α/pDY18, E. coli/pRK2013 and A. tumefaciens MP90 were mixed together and a 100 µl of the mixture incubated overnight at 28° C. on agar plates containing yeast and tryptone extracts (2YT) with no antibiotics. The cultures were then diluted in 10 mM MgSO$_4$ and incubated on minimal media containing kanamycin (25 µg/ml) and gentomycin (25 µg/ml) to select for A. tumefaciens/pDY18.

EXAMPLE 3

Selection of ADA Transformed Plant Cells and Regenerated plants on Ara-A and Cordycepin Containing Media.

Leaf discs cut from *Nicotiana tabacum* cv. Xanthi were soaked in a dilution of an overnight culture of Agrobacterium/pDY18 for several seconds, blotted dry and placed on Murashige and Skoog medium containing Gamborg's (MS/B5 medium containing 30 g/l sucrose, 2 mg/l 2,4-dichlorophenoxy acetic acid and 7% phytoagar). After 2 days of co-cultivation the leaf discs were placed on medium containing ara-A (100 µM) or cordycepin (50 µM) as selective agents and 500 µg/ml carbenicillin to inhibit Agrobacterium growth. The shoots which were regenerated were transferred to rooting medium containing MS basal medium containing Gamborg's vitamins (MS/B5, Sigma), 30 g/l sucrose, 0.1 mg/l a-naphthalene acetic acid (NAA), 500 µg/ml carbenicillin and 100 µg/ml kanamycin and 6 g/l phytoagar, adjusted to pH 5.6. Regenerated plants were transferred to soil and grown at 25° C. in an 18/6 hrs day/night cycle. Two plants designated 18-2 and 18-3 were chosen for further study.

Leaf discs cut from plant 18-2, 18-3, and Normal (non-transformed) plants were cultured on agar MS agar media containing either no selective agent or ara-A (100 µM) or cordycepin (50 µM). On the media containing no selective agent, tissues derived from both 18-2 and non-transformed plants proliferated, while on media containing either ara-A at 100 µM or cordycepin at 50 µM, only the tissues derived from transformed plant 18-2 proliferated. Tissues derived from plant 18-3 also proliferated on media containing either ara-A or cordycepin. No growth was observed with tissues from non-transformed (Normal) plants on media containing either ara-A or cordycepin, respectively. These observations established the potential use of the ADA gene as a selectable gene in plant tissue and plant cell transformation systems.

EXAMPLE 4

Demonstration of the Presence of the ADA gene in Transformed Plants Using Polymerase Chain Reaction (PCR).

To demonstrate that the ADA gene was actually present in the genomic DNA of transformed plants, DNA was extracted from A. tumefaciens/pDY18, transformed plant 18-2 (produced as in Example 3 above) and non-transformed plants using standard phenol extraction procedures (Edwards et. al., *Nucleic Acid Research* 19: 1349, 1911; the disclosure of which is incorporated herein by reference). A 6 mm leaf disc was ground for 15 sec. at room temperature (RT) without buffer and then 400 µl of extraction buffer (200 mM Tris-HCl pH 7.5, 250 mM NaCl, 25 mM EDTA, 0.5% SDS) was added and then vortexed for 5 seconds. The extract was centrifuged for 1 minute at 13,000 rpm. Three hundred μl of the supernatant was transferred to a new centrifuge tube and 300 μl of isopropanol added to precipitate the DNA. After 2 min. at RT the sample was centrifuged at 13,00 rpm for 5 min. to pellet the DNA. The pellet was washed with 70% ethanol, dried and dissolved in 100 μl Tris-HCL pH 7.5. Adenosine deaminase gene specific polymerase chain reaction (PCR) oligonucleotide primers were synthesized on an Applied Biosystems 394 DNA/RNA synthesizer. The columns, phosphoramidites and reagents used for oligonucleotide synthesis were all obtained from Applied Biosystems. The two PCR primers were based on the published sequence of the mouse ADA gene [SEQ ID NO:1]. Primer ADA-1 corresponds to the 5' coding sequence of the ADA gene, bases 1–13 (5' atggcccagacacc 3') [SEQ ID NO:3], primer ADA-2 complementary to the 3' coding sequence of the ADA gene, bases 1038–1060 (5' ctattggtat-tctctgtagagc 3') [SEQ ID NO:4]. PCR reactions mixtures (100 μl) contained ADA-1 and ADA-2 (1 μg each), 20 mM Tris HCL (pH8.8), 10 mM KCl, 10 mM $(NH_4)_2SO_4$, 2 mM $MgSO_4$, 0.1% Triton-X 100, 1 mM dNTPs (dATP, dCTP, dGTP, dTTP) and 2.5 units Taq DNA polymerase (Gibco/BRL). Reaction mixtures were heated to 96° C. for 2 minutes and then subjected to 35 cycles of the following temperature regains 94° C. for .30 seconds, 60° C. for 30 seconds, and 72° C. for 2 minutes. Nine μl of each reaction mixture were then subjected to electrophoresis on 1% agarose.

Figure 2:
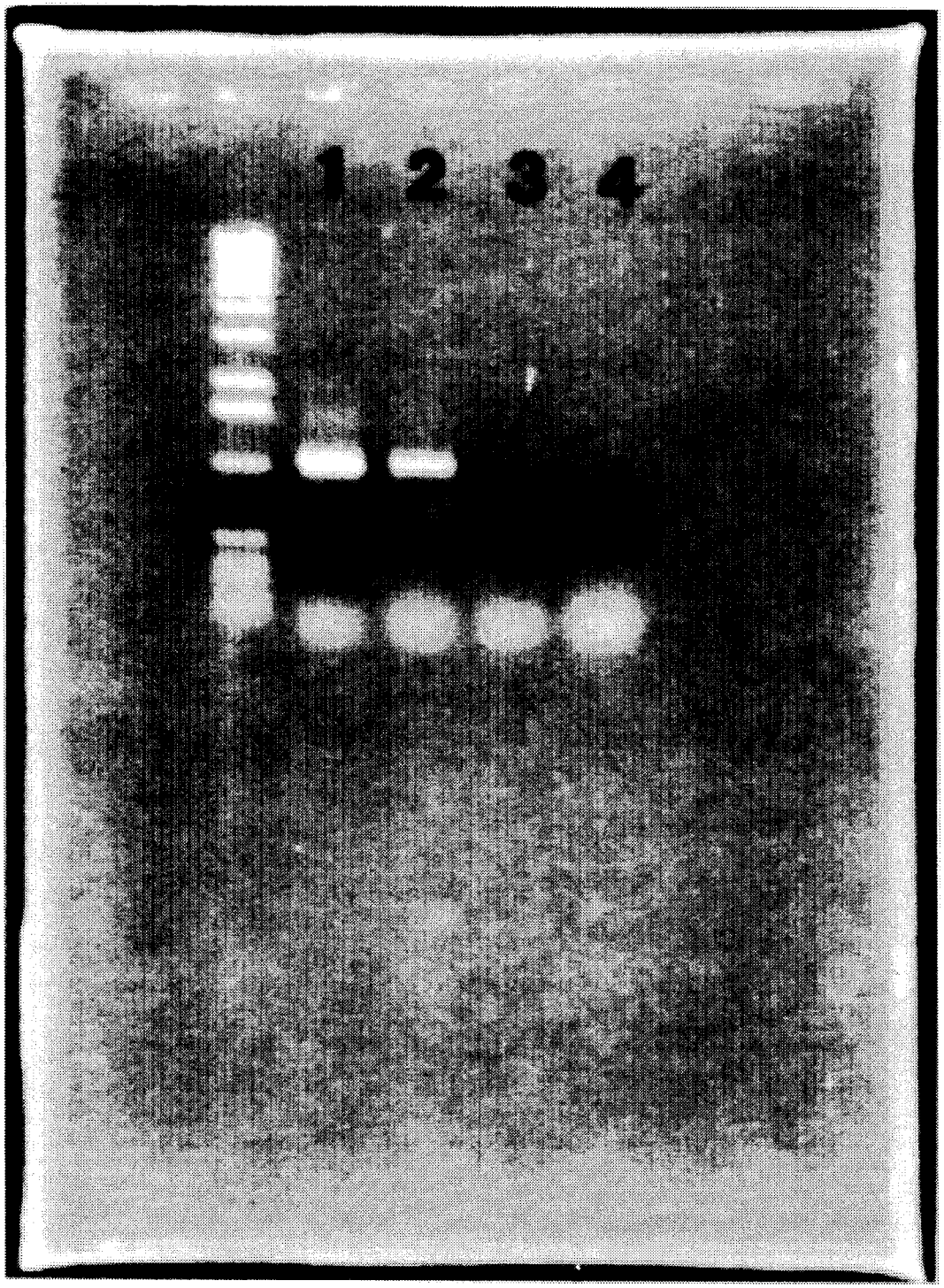
FIG. 2 is an electrophorogram carried out on mixtures resulting from polymerase chain reaction experiments described in Example 4 below.

FIG. 2 demonstrates the presence of the ADA gene as a 1.06 Kb band when using plasmid (pDY18) extracted from A. tumefaciens as a control and in the DNA extracted fromtransformed plant 18-2, but not when using DNA from non-transformed tobacco or Brassica plants. In the electrophorogram, Lane 1 is a plasmid (pDY18) control, Lane 2 is transformed tobacco, Lane 3 is non-transformed tobacco and Lane 4 is non-transformed brassica.

EXAMPLE 5

The Colorimetric Detection and Analysis of Adenosine Deaminase in Transformed Plants and Plant Cells.

To assay for adenosine deaminase activity in leaf tissues, 6 mm leaf discs or portions thereof (½, ¼, ⅛) were placed in wells of a microtitre dish and incubated in 50 μl adenosine solution (50 mM adenosine, 50 mM phosphate buffer <pH 7.5>) for 30 or 60 min. at 37° C. Fifty μl phenol/nitroprusside solution (106 mM phenol, 0.17 mM sodium nitroprusside) and 50 μl alkaline hypochlorite (600 mM sodium hydroxide, 0.125% sodium hypochlorite) were added and incubated in the dark at 37° C. for 30 minutes to allow for color development.

Incubation mixtures containing tissues from ADA gene transformed plants (18-2, 18-3 as produced in Example 3) developed an intense blue color while those with tissues from non-transformed plants (Normal) or with tissues from a plant transformed with a gene other than ADA, the herbicide resistance gene phosphinothricine acetotransferase (N[PAT]), remained colorless or only faintly blue.

Incubation mixtures containing leaf, stem or callus tissues from ADA transformed plants (18-2, 18-3) developed a blue color while the corresponding tissues from non-transformed plants remained colorless.

To further demonstrate that the color development was dependent on ADA activity in the transformed tissue the effect of increasing concentrations of 2'-deoxycoformycin, a specific inhibitor of adenosine deaminase (Philips et. al., *Biochemistry* 26: 2893–2903, 1987; the disclosure of which is incorporated herein by reference) was studied. Leaf tissues, ⅛ sections of 6 mm leaf discs, from ADA transformed (18-2) and non-transformed (Normal) plants were incubated in 50 μl adenosine solution (50 μM) containing either 1 μl, 4 μ, or 7 μl 2'-deoxycoformycin at 10 μM, 1 μM, 100 nM, 10 nM, or 100 pM concentration. After incubation, phenol/nitroprusside and alkaline hypochlorite solutions were added as described above. Increasing concentrations of deoxycoformycin prevented color development by inhibiting ADA activity in transformed leaf tissues (18-2). A control involved reaction mixtures from transformed (18-2) and non-transformed (Normal) without deoxycoformycin added. These showed the expected color generation (18-2) or no color (Normal).

EXAMPLE 6

Colorimetric assays of ADA activity.

To assay for adenosine deaminase activity in leaf tissue, ½ and ⅛ portions of 6 mm leaf discs of tissues 18-2, 18-3, Normal and N[PAT] as indicated above, were placed in wells of a microtitre dish and incubated in 50 μl solution (50 mM adenosine) for 60 min at 37° C. and then either 50 μl bromthymol blue (20 mg/100 ml, pH 5.6 or 6.8) or 50 μl phenol red (20 mg/100 ml, pH 5.6 or 6.8) was added to detect the increase in pH of the reaction medium resulting from ammonia liberation as a result of adenosine deaminase activity.

The conversion of adenosine to inosine and ammonia by adenosine deaminase caused the pH indicator bromthymol blue (Blue) to change from clear to dark blue and the pH indicator phenol red (Red) to change from yellow to red in transformed tissue (18-2 and 18-3), whereas with non-transformed (Normal) and (N[PAT]) tissues the pH indicators remained clear or yellow, respectively. The sensitive range for bromthymol blue is pH 6.0–7.6 and for phenol red pH 6.8–8.4. This may account for the apparent greater sensitivity of bromthymol blue (⅛) as compared to phenol red (⅛) observed in the results.

What I claim is:

1. A genetically transformed plant cell containing foreign genetic material, said foreign genetic material including a gene expressing an adenosine deaminase enzyme.

2. A plant cell according to claim 1 wherein said gene is a mouse adenosine deaminase gene.

3. A plant cell according to claim 2 wherein said gene has the nucleotide sequence of SEQ ID NO:2.

4. A plant cell according to claim 1 containing a further foreign gene.

5. A genetically transformed plant cell containing foreign genetic material, including a gene of mouse origin expressing adenosine deaminase.

6. A process of genetic transformation of plant cells, comprising:
preparing plant cells for transformation;
introducing a vector containing foreign DNA, including a gene expressing an adenosine deaminase enzyme, into said plant cells to form a mixture of cells containing successfully transformed cells and other cells;

selecting said successfully transformed plant cells by culturing said cell mixture in a medium containing deoxyadenosine or an analog thereof at a concentration that inhibits normal plant cells and collecting plant cells that are not substantially inhibited; and amplifying said successfully transformed plant cells.

7. A process according to claim 6 wherein said analog of deoxyadenosine is selected from the group consisting of 2-deoxyadenosine, 3-deoxyadenosine, 9-B-D-arabinofuranosyl adenine, 9-B-D-xylofuranosyl adenine, 2,6-diaminopurine riboside, 6-chloropurine riboside, 6-methoxypurine riboside, and 2'-3'-dideoxyadenosine and 2-chloroadenosine.

8. A process according to claim 6 wherein said vector is introduced into said plant cells via Agrobacterium sp. containing said vector.

9. A process according to claim 6 wherein said vector is introduced into said plant cells by micro-projectile bombardment.

10. A process according to claim 6 wherein a presence of said gene is confirmed in said collected or amplified plant cells by culturing said cells in a medium containing adenosine or an analog thereof and a compound that changes color in the presence of ammonia, and observing a change of said color as confirmation of said presence.

11. A vector for introducing foreign DNA into plant cells comprising plant regulatory sequences operably linked to a gene expressing an adenosine deaminase enzyme.

12. A vector according to claim 11 wherein said gene comprises a mouse adenosine deaminase gene.

13. A vector according to claim 11 wherein said gene comprises the nucleotide sequence of SEQ ID NO:2.

14. The plasmid pRD360-ADA (ATCC 69459).

15. A plant cell according to claim 3, being a transformant of a member of the family Solonaceae.

16. A plant cell according to claim 3, being a transformant of a genotype of tobacco (Nicotinia).

17. A plant cell according to claim 3, being a transformant of *Nicotinia tabacum* cv. Xanthi.

18. A process according to claim 6 wherein said plant cells are derived from a strain of tobacco.

19. A process according to claim 18 wherein said gene has the nucleotide sequence of SEQ ID NO:2.

20. A plant cell according to claim 3, being a transformant of a genotype of Brassica.

* * * * *